(12) United States Patent
Kurz

(10) Patent No.: US 6,579,317 B2
(45) Date of Patent: Jun. 17, 2003

(54) ARRANGEMENT FOR COUPLING HEARING IMPLANT

(75) Inventor: Heinz Kurz, Dusslingen (DE)

(73) Assignee: Heinz Kurz GmbH Medizintechnik, Dusslingen (DE)

(*) Notice: Subject to any disclaimer, the term of this patent is extended or adjusted under 35 U.S.C. 154(b) by 21 days.

(21) Appl. No.: 09/933,619

(22) Filed: Aug. 21, 2001

(65) Prior Publication Data
US 2002/0045939 A1 Apr. 18, 2002

(30) Foreign Application Priority Data
Aug. 24, 2000 (DE) .......................... 200 14 659

(51) Int. Cl.⁷ .......................... A61F 2/18; H04R 25/00
(52) U.S. Cl. .......................... 623/10; 600/25
(58) Field of Search .......................... 623/10; 600/25; 607/55–57

(56) References Cited

U.S. PATENT DOCUMENTS

| 5,015,225 A | | 5/1991 | Hough et al. | |
|---|---|---|---|---|
| 5,941,814 A | * | 8/1999 | Lehner et al. | 600/25 |
| 6,168,625 B1 | * | 1/2001 | Prescott | 623/10 |
| 6,277,148 B1 | * | 8/2001 | Dormer | 623/10 |
| 6,387,038 B1 | * | 5/2002 | Kroll et al. | 600/25 |
| 6,387,128 B1 | * | 5/2002 | Kurz et al. | 623/10 |
| 6,398,717 B1 | * | 6/2002 | Leysieffer et al. | 600/25 |
| 6,432,139 B1 | * | 8/2002 | Elies et al. | 623/10 |

FOREIGN PATENT DOCUMENTS

| DE | 297 18 091 U1 | 1/1998 |
|---|---|---|
| DE | 197 44 789 A1 | 4/1998 |
| DE | 197 38 587 C1 | 6/1999 |
| DE | 199 48 375 A1 | 5/2001 |
| EP | 1 054 573 A2 | 11/2000 |

* cited by examiner

Primary Examiner—David H. Willse
Assistant Examiner—Suzette J. Jackson
(74) Attorney, Agent, or Firm—Michael F. Striker (57) ABSTRACT

An arrangement for coupling at least partially a hearing device implantable in a middle ear or a passive auditory ossicles prosthesis on an ascending bracket of a human ossicle chain, the arrangement has a body, and a clip provided on the body and formed so as to automatically mount on an ascending bracket.

12 Claims, 6 Drawing Sheets

ARRANGEMENT FOR COUPLING HEARING IMPLANT

BACKGROUND OF THE INVENTION

The present invention relates to an arrangement for coupling a hearing implant which is at least partially implantable in a middle ear or a passive auditory ossicles prosthesis on an ascending bracket of a human ossicle chain.

Nowadays both active and passive hearing implants are mounted on an auditory ossicles by mounting elements formed as a sleeve and subsequently the mounting element is fixed by a crimping tool on the auditory ossicle permanently. Such a mounting method is disclosed for example in the German patent document DE 197 38 587. These known mounting possibilities for middle ear prostheses or hearing devices are however relatively expensive. After fitting the sleeve-shaped mounting element on the auditory ossicles, a crimping tool must be exactly placed to provide a position-accurate and reliable mounting of the implant.

SUMMARY OF THE INVENTION

Accordingly, it is an object of the present invention to provide an arrangement for coupling a hearing implant, which makes possible mounting of both active and passive hearing implants in a simple manner and with a guarantee of reliable hold of the prosthesis.

In keeping with these objects and with others which will become apparent hereinafter, one feature of present invention resides, briefly stated, in an arrangement for coupling a hearing device which is implantable at least partially in a middle ear, or a passive auditory ossicle prosthesis on an ascending bracket of a human ossicle chain, which in accordance with the present invention has a clip mountable automatically on the ascending bracket.

When the arrangement is provided with the clamp, then the active or passive hearing implant can be mounted without the use of tool, fast and reliable on the ascending bracket. The clip can have spring tongs which are axially displaceable over the ascending bracket. An especially reliable hold is guaranteed when the clip engages around the ascending bracket at four sides.

Since the sides at the relative position of the auditory ossicles for each person is different, it is advantageous when the clip has a movable connection to a hearing device or an auditory ossicles prosthesis. Then an adjustment of the prosthesis or the hearing device of the corresponding characteristics in the middle ear is possible in situ. The movable connection can be performed for example by a shaft of a flexible material. It is however possible to provide a spherical joint between the clip and the hearing device or the prosthesis.

In accordance with another feature of the present invention, the clip can be formed of one piece of the hearing device or the auditory ossicles prosthesis for a connection with a flexible shaft. It forms in this case one end of the prosthesis or the hearing device implant.

The clip connection, whether in form of a flexible shaft or a spherical joint, can be mounted by means of a plug or clamp connection on the hearing device or the auditory ossicles prosthesis.

The whole coupling arrangement can be composed of a biocompatible material, such as titanium or a titanium alloy, to prevent rejection reactions of the body.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
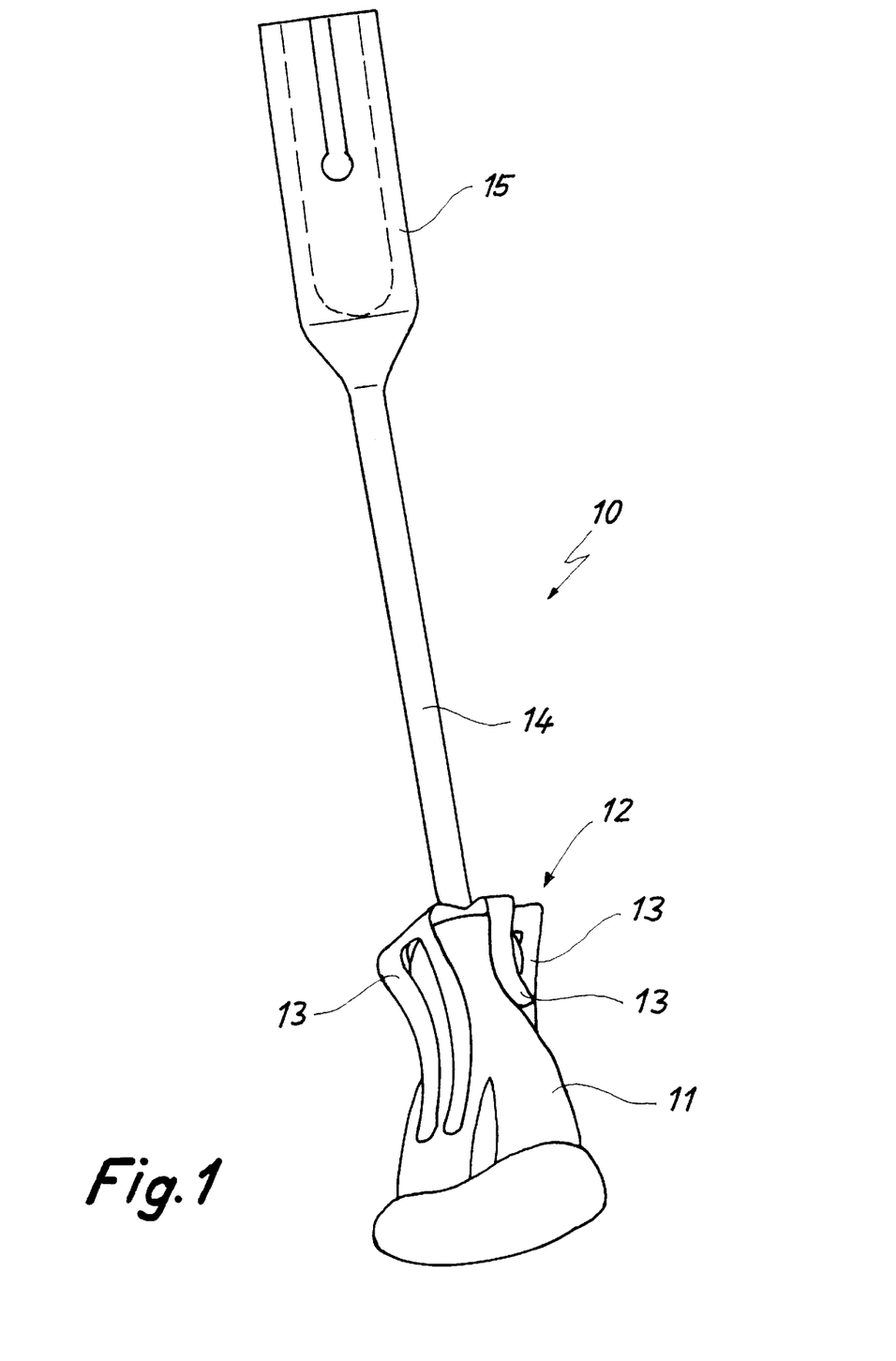
FIG. 1 is a perspective view of a coupling device in accordance with the first embodiment of the present invention.

FIG. 1 is a view showing a first coupling arrangement 10 for coupling of a not shown hearing implant on an ascending bracket 11 of a human ossicles chain. The coupling arrangement 10 has a clip 12 provided on its lower end and having several springy tongs 13. The tongs are displaceable in an axial direction over the ascending bracket 11 and engage around the ascending bracket 11 from four sides. A shaft 14 extends from the clip 12 and is composed of a flexible material. It transits into a plug sleeve 15. The actuator of an active hearing implant or the shaft of an auditory ossicles prosthesis is for example anchorable in the plug sleeve 15. The flexible shaft 14 makes possible an adaptation of the position of the total prosthesis to the specific anatomical characteristics of the patient.

Figure 2:
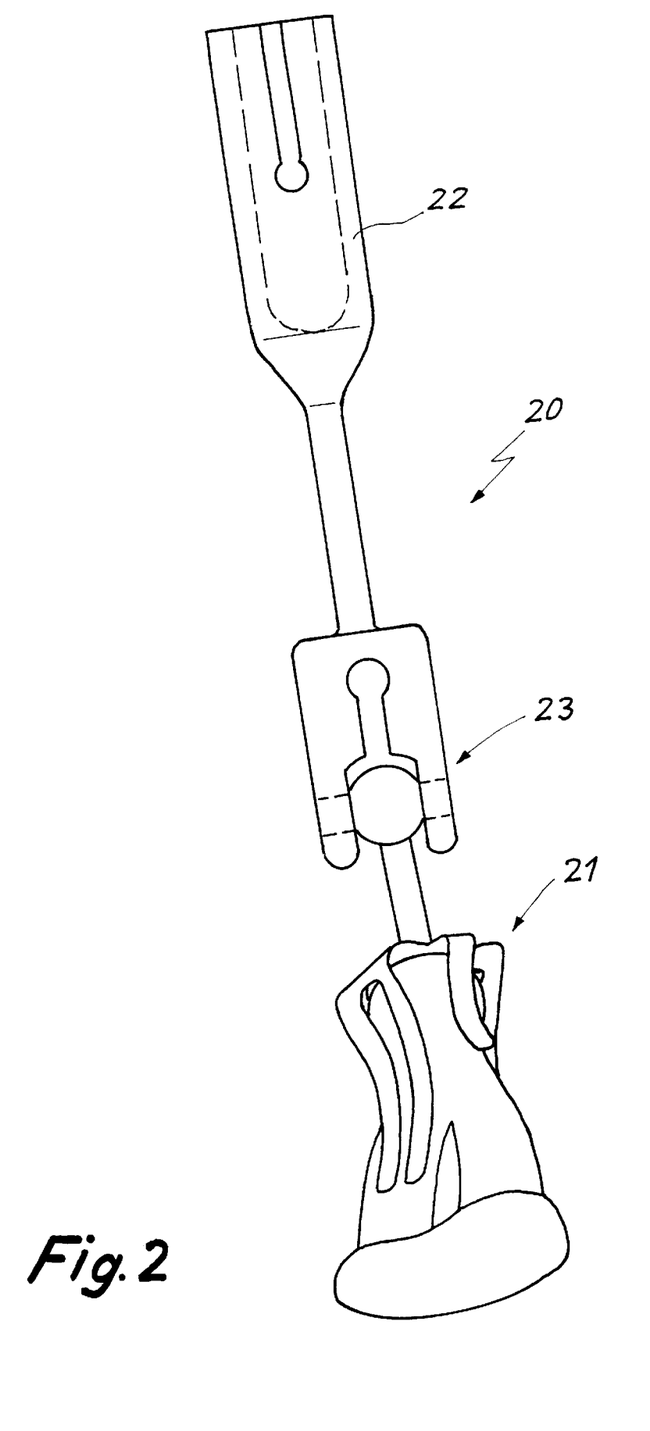
FIG. 2 is a perspective view of a coupling device in accordance with the second embodiment of the present invention.

FIG. 2 shows a coupling device 20. On its lower end it also has a springy clip 21 of the same construction as the clip 12 in FIG. 1. On the upper end it also has a plug sleeve 22 which corresponds in its appearance to the sleeve 15 of FIG. 1. The coupling device 20 is different from the coupling device 10 by a movable connection between the sleeve 22 and the clip 21. This movable connection is performed here not by the flexible shaft, but instead by a spherical joint 23.

Figure 3:
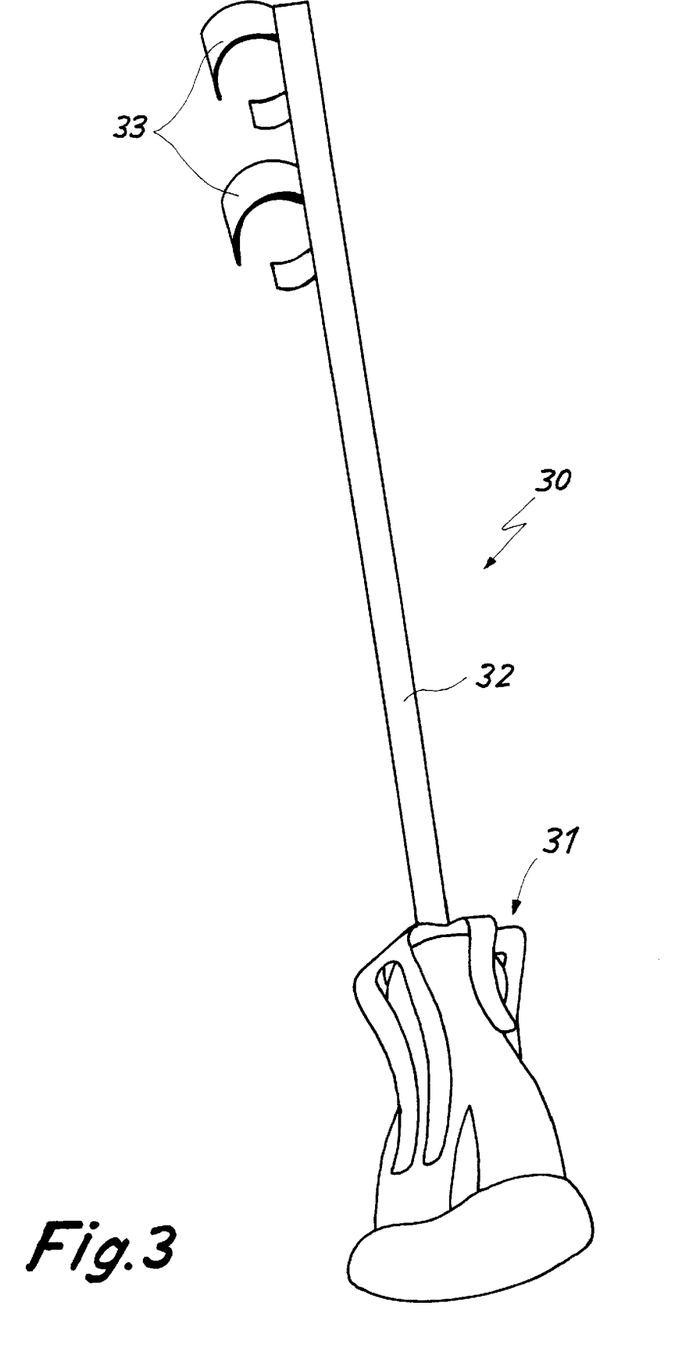
FIG. 3 is a perspective view of a coupling device in accordance with the third embodiment of the present invention.

FIG. 3 shows a coupling device 30 which is similar to the coupling device 10 of FIG. 1. Here however a springy clip 31 is provided which has the same construction as the clip 10 of FIG. 1. A shaft 32 of a flexible material extends from the clip. In the coupling device 30 the coupling on the hearing implant is not performed by a plug sleeve, but instead by clamps 33 and the clamping action of these clamps.

Figure 4:
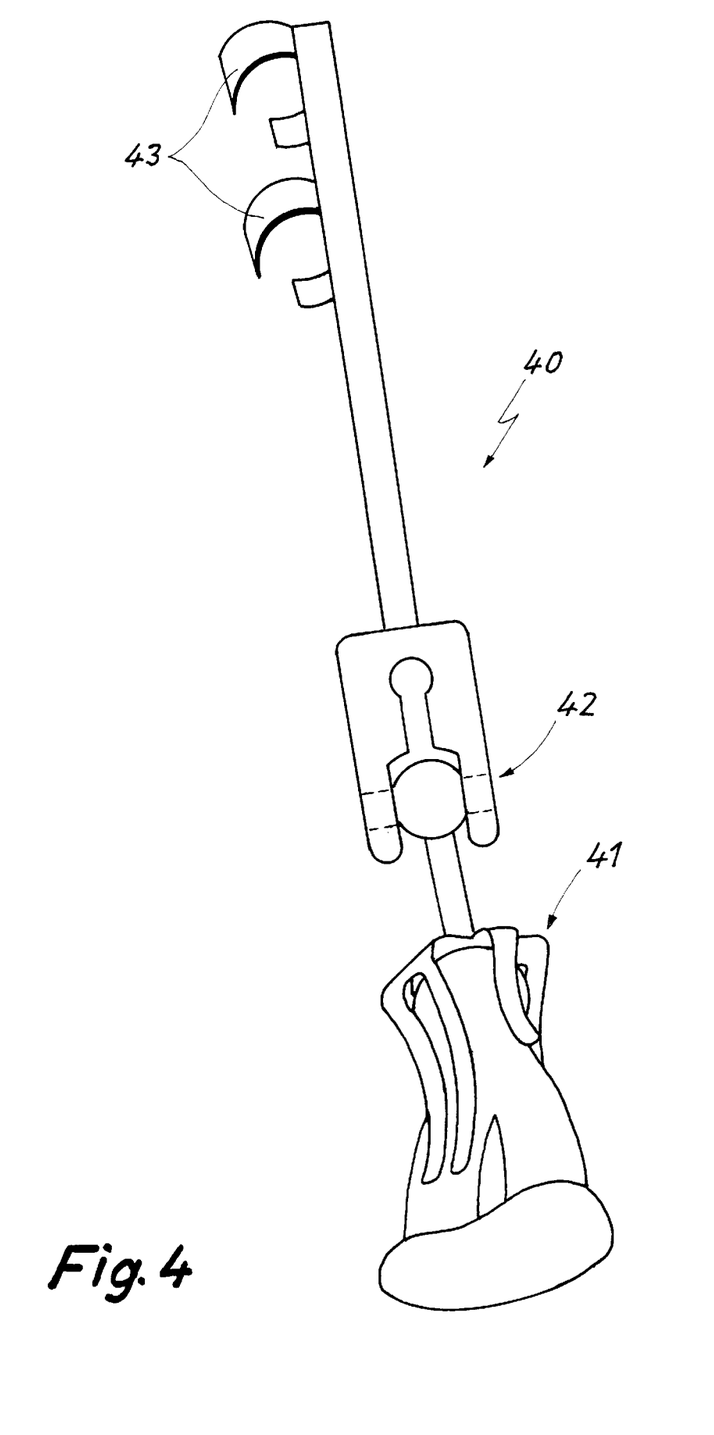
FIG. 4 is a perspective view of a coupling device in accordance with the fourth embodiment of the present invention.

FIG. 4 shows a coupling device 40 which substantially corresponds to the coupling device shown in FIG. 3. Here however the flexible shaft 32 is replaced by a spherical joint 42. The mounting of the coupling device on the prosthesis is performed here also by clamps 43.

Figure 5:
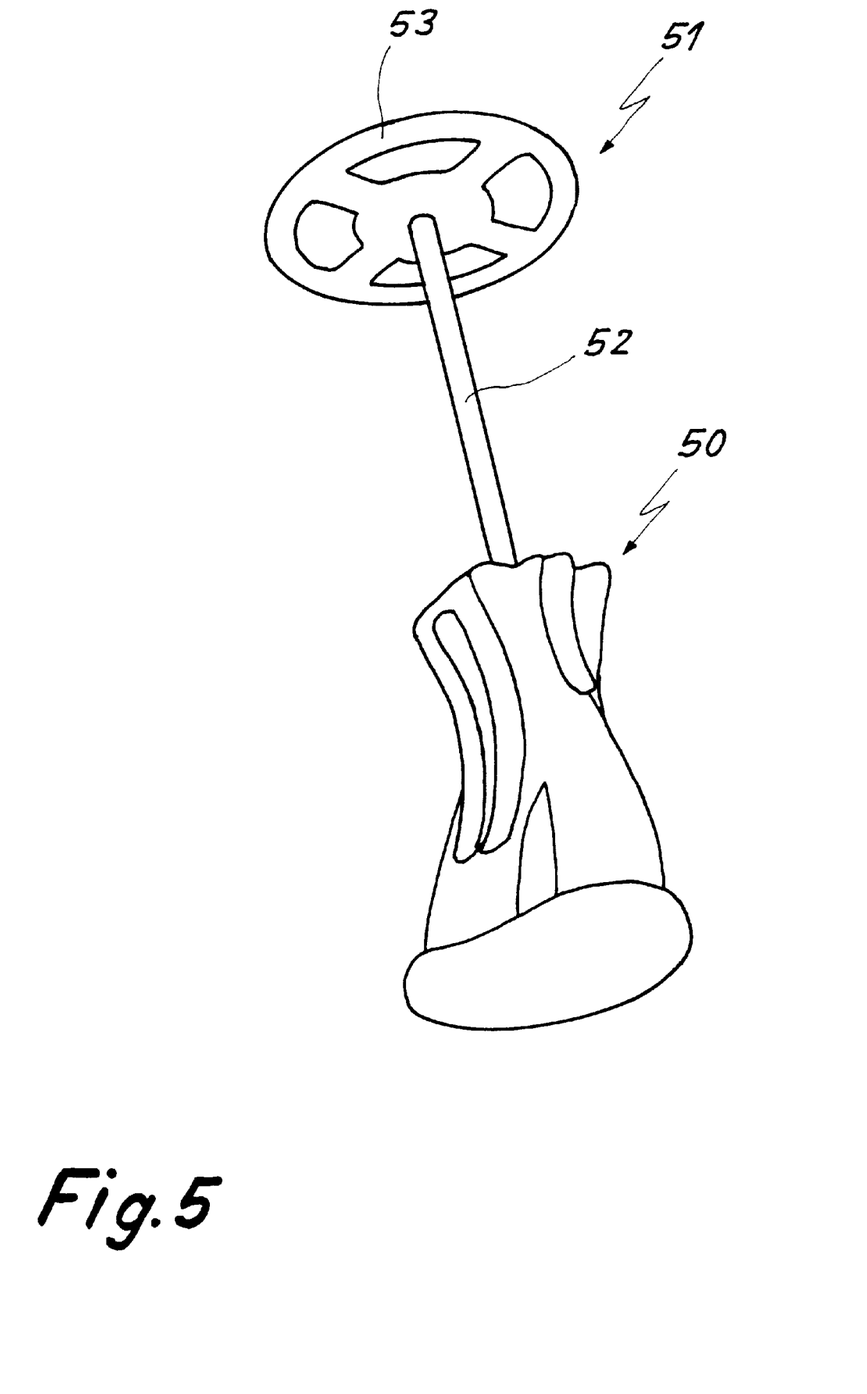
FIG. 5 is a perspective view of a coupling arrangement which is formed of one piece with a prosthesis.

FIG. 5 shows a coupling device 50 for an auditory ossicles prosthesis 41. In this case it is composed strictly of the springy clip of the same type as the clip 12 of FIG. 1. A shaft 52 which is connected to the clip 50 forms simultaneously the shaft of the prosthesis 51 and can be composed for example of a flexible material. On the opposite end of the shaft 52, a grating plate 53 is arranged. It is brought in abutment against the eardrum skin.

Figure 6:
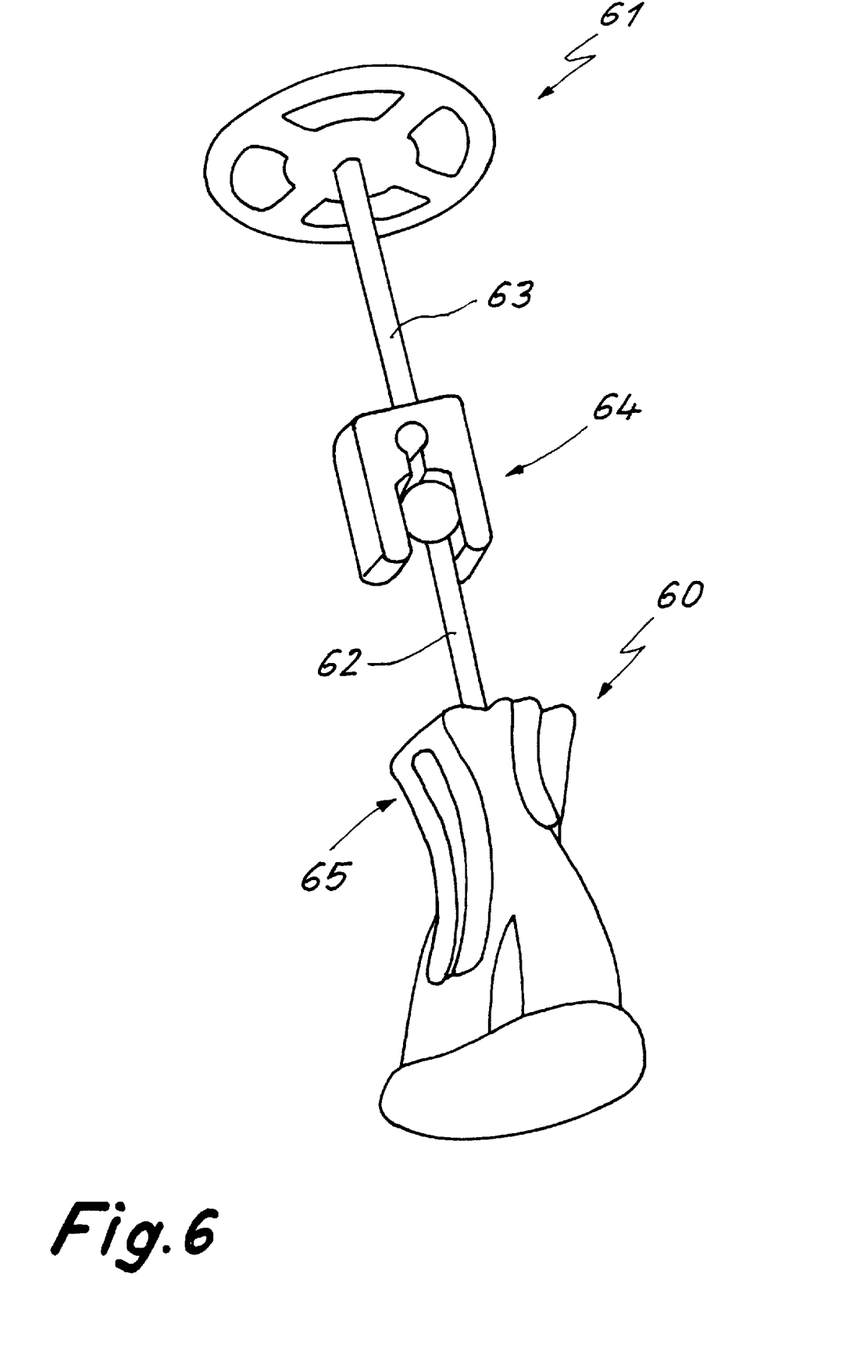
FIG. 6 is a perspective view of a coupling arrangement with an auditory ossicles prosthesis.

A completely similar coupling device 60 for a prosthesis 61 is shown in FIG. 6. Here however both the shaft 62 of the coupling device 60 and the shaft 63 of the prosthesis 61 are composed of a rigid material. In order however to provide a flexible adjustment of the prosthesis 61 to the anatomical characteristics of the patient, a spherical joint 64 is arranged between the shafts 62 and 63.

It will be understood that each of the elements described above, or two or more together, may also find a useful application in other types of constructions differing from the types described above.

While the invention has been illustrated and described as embodied in arrangement for coupling hearing implant, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. An arrangement for coupling at least partially a hearing device implantable in a middle ear or a passive auditory ossicles prosthesis on an ascending bracket of a human ossicle chain, the arrangement comprising a body, and a clip provided on said body and formed so as to automatically mount on an ascending bracket, said clip having a plurality of spring tongs which are axially displaceable over the ascending bracket.

2. An arrangement as defined in claim 1, wherein said clip is formed so as to engage the ascending bracket from four sides.

3. An arrangement as defined in claim 1, wherein said clip is formed so as to provide a movable connection to a hearing device or to an auditory ossicles prosthesis.

4. An arrangement as defined in claim 3, wherein said body has a spherical joint which provides said movable connection.

5. An arrangement as defined in claim 1, wherein said body has means for clamping connection with the hearing device or the auditory ossicles prosthesis.

6. An arrangement as defined in claim 1, wherein the arrangement is composed of a biocompatible material.

7. An arrangement as defined in claim 6, wherein the arrangement is composed of titanium.

8. An arrangement as defined in claim 6, wherein the arrangement is composed of a titanium alloy.

9. An arrangement for coupling at least partially a hearing device implantable in a middle ear or a passive auditory ossicles prosthesis on an ascending bracket of a human ossicle chain, the arrangement comprising a body, and a clip provided on said body and formed so as to automatically mount on an ascending bracket said clip being formed so as to provide a movable connection to a hearing device or to an auditory ossicles prosthesis, said body having a shaft which is composed of flexible material and provides said movable connection.

10. An arrangement for coupling at least partially a hearing device implantable in a middle ear or a passive auditory ossioles prosthesis on an ascending bracket of a human ossicle chain, the arrangement comprising a body, and a clip provided on said body and formed so as to automatically mount on an ascending bracket said body being formed of one piece with the hearing device.

11. An arrangement for coupling at least partially a hearing device implantable in a middle ear or a passive auditory ossicles prosthesis on an ascending bracket of a human ossicle chain, the arrangement comprising a body, and a clip provided on said body and formed so as to automatically mount on an ascending bracket, said body is formed of one piece with the auditory ossicles prosthesis.

12. An arrangement for coupling at least partially a hearing device implantable in a middle ear or a passive auditory ossicles prosthesis on an ascending bracket of a human ossicle chain, the arrangement comprising a body, and a clip provided on said body and formed so as to automatically mount on an ascending bracket, said body has means for plug connection with the hearing device or the auditory ossicles prosthesis.

* * * * *

US006579317C1

(12) INTER PARTES REEXAMINATION CERTIFICATE (956th)
United States Patent
Kurz (10) Number: US 6,579,317 C1
(45) Certificate Issued: Sep. 5, 2014

(54) ARRANGEMENT FOR COUPLING HEARING IMPLANT

(75) Inventor: Heinz Kurz, Dusslingen (DE)

(73) Assignee: Heinz Kurz GmbH Medizintechnik, Dusslingen (DE)

Reexamination Request:
No. 95/000,662, Apr. 2, 2012

Reexamination Certificate for:
Patent No.: 6,579,317
Issued: Jun. 17, 2003
Appl. No.: 09/933,619
Filed: Aug. 21, 2001

(30) Foreign Application Priority Data

Aug. 24, 2000 (DE) .................................. 200 14 659

(51) Int. Cl.
*A61F 2/18* (2006.01)
*H04R 25/00* (2006.01)

(52) U.S. Cl.
USPC ............................................... 623/10; 600/25

(58) Field of Classification Search
None
See application file for complete search history.

(56) References Cited

To view the complete listing of prior art documents cited during the proceeding for Reexamination Control Number 95/000,662, please refer to the USPTO's public Patent Application Information Retrieval (PAIR) system under the Display References tab.

*Primary Examiner* — Jeffrey R Jastrzab (57) ABSTRACT

An arrangement for coupling at least partially a hearing device implantable in a middle ear or a passive auditory ossicles prosthesis on an ascending bracket of a human ossicle chain, the arrangement has a body, and a clip provided on the body and formed so as to automatically mount on an ascending bracket.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-12 are cancelled.

\* \* \* \* \*